United States Patent
Cros et al.

(10) Patent No.: US 9,180,057 B2
(45) Date of Patent: Nov. 10, 2015

(54) MADE-TO-MEASURE ORTHOSIS FOR COMPRESSION/CONTAINMENT, FOR REINFORCING THE MUSCULO-APONEUROTIC PUMP OF THE CALF

(75) Inventors: Francois Cros, Ivry sur Seine (FR); Pauline Rafstedt, Nancy (FR)

(73) Assignee: Innothera Topic International, Arcueil (FR)

( * ) Notice: Subject to any disclaimer, the term of this patent is extended or adjusted under 35 U.S.C. 154(b) by 803 days.

(21) Appl. No.: 13/289,125

(22) Filed: Nov. 4, 2011

(65) Prior Publication Data

US 2012/0116282 A1     May 10, 2012

(30) Foreign Application Priority Data

Nov. 10, 2010 (FR) ...................... 10 59288

(51) Int. Cl.
| | |
|---|---|
| A41D 13/00 | (2006.01) |
| A41D 13/06 | (2006.01) |
| A41D 27/12 | (2006.01) |
| A41B 11/00 | (2006.01) |
| A41B 11/02 | (2006.01) |

(Continued)

(52) U.S. Cl.
CPC ............... *A61F 13/08* (2013.01); *A41B 11/00* (2013.01); *A41B 11/02* (2013.01); *A41B 11/12* (2013.01); *A41D 13/015* (2013.01); *A41D 13/018* (2013.01); *A41D 13/081* (2013.01); *A61F 5/00* (2013.01); *A61F 9/00* (2013.01); *A61F 9/04* (2013.01); *A61F 13/00* (2013.01); *A61F 13/02* (2013.01); *A61F 13/0273* (2013.01); *A61F 13/06* (2013.01); *A61F 13/061* (2013.01); *A61F 13/107* (2013.01); *A61F 13/14* (2013.01); *A61M 25/02* (2013.01)

(58) Field of Classification Search
CPC ............... A61F 5/00; A61F 9/00; A61F 9/04; A61F 13/00; A61F 13/02; A61F 13/0273; A61F 13/06; A61F 13/061; A61F 13/08; A61F 13/107; A61F 13/14; A61M 25/02; A61D 13/015; A61D 13/018; A61D 13/081; A61B 11/00; A61B 11/12; A61B 11/02
USPC .......... 128/846, 869, 882; 602/60–61, 75–76; 2/456, 22, 61, 239–242
See application file for complete search history.

(56) References Cited

U.S. PATENT DOCUMENTS 3,386,270 A * 6/1968 Simmons .................... 66/178 A
5,364,686 A * 11/1994 Disselbeck et al. ........... 428/174
(Continued)

FOREIGN PATENT DOCUMENTS

| EP | 1240880 | 9/2002 |
|---|---|---|
| EP | 2050848 | 4/2009 |
| FR | 2824471 | 11/2002 |

*Primary Examiner* — Alireza Nia
*Assistant Examiner* — Brandon L Jackson
(74) *Attorney, Agent, or Firm* — Jacobson Holman PLLC

(57) ABSTRACT

The orthosis comprises an elastic compressive distal portion extending upwards from the ankle and associated with an adjoining containment proximal portion covering a region of the calf extending between the level of the junction point between the Achilles tendon and the calf muscle and the level situated beneath the tibial tuberosity. This containment proximal portion is an essentially non-elastic deformable tubular portion made by knitting with a thermoformable yarn, and it is knitted continuously with the elastic compressive distal portion.

3 Claims, 2 Drawing Sheets

(51) Int. Cl.

| | |
|---|---|
| A62B 17/00 | (2006.01) |
| A61F 5/37 | (2006.01) |
| A61B 19/00 | (2006.01) |
| A61L 15/00 | (2006.01) |
| A61F 13/08 | (2006.01) |
| A61F 13/14 | (2006.01) |
| A61F 13/02 | (2006.01) |
| A61F 13/10 | (2006.01) |
| A61F 13/00 | (2006.01) |
| A61F 9/04 | (2006.01) |
| A61F 5/00 | (2006.01) |
| A61M 25/02 | (2006.01) |
| A61F 9/00 | (2006.01) |
| A61F 13/06 | (2006.01) |
| A41D 13/08 | (2006.01) |
| A41D 13/015 | (2006.01) |
| A41D 13/018 | (2006.01) |
| A41B 11/12 | (2006.01) |

(56) References Cited

U.S. PATENT DOCUMENTS

| | | | |
|---|---|---|---|
| 6,820,406 B2 * | 11/2004 | Khavkine et al. | 57/120 |
| 2003/0157323 A1 * | 8/2003 | Khavkine et al. | 428/373 |
| 2009/0240279 A1 * | 9/2009 | Becker et al. | 606/201 |

* cited by examiner

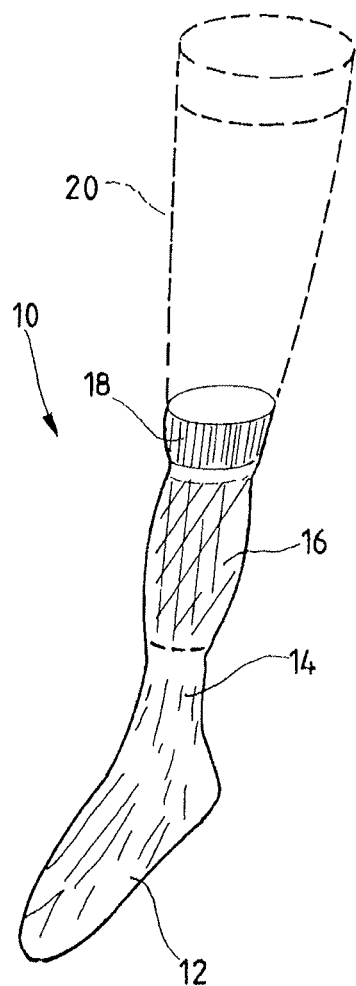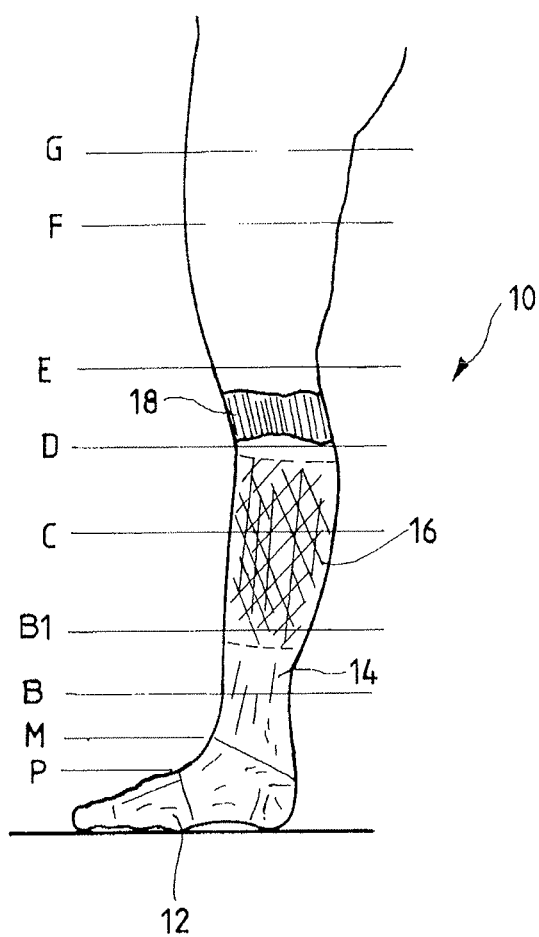
FIG_1    FIG_2

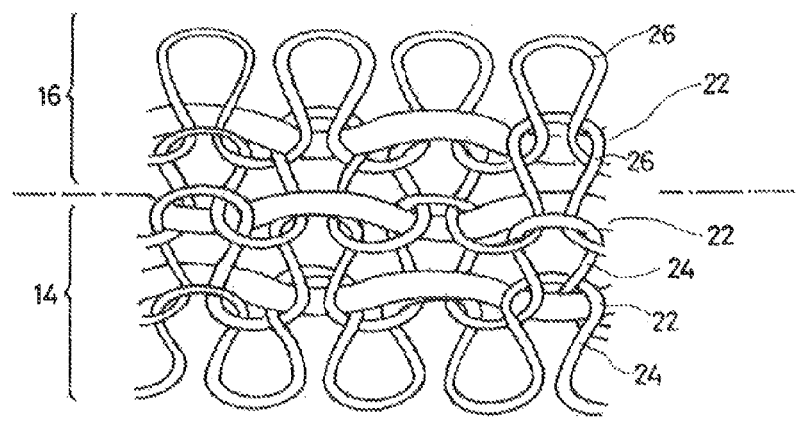
FIG_3
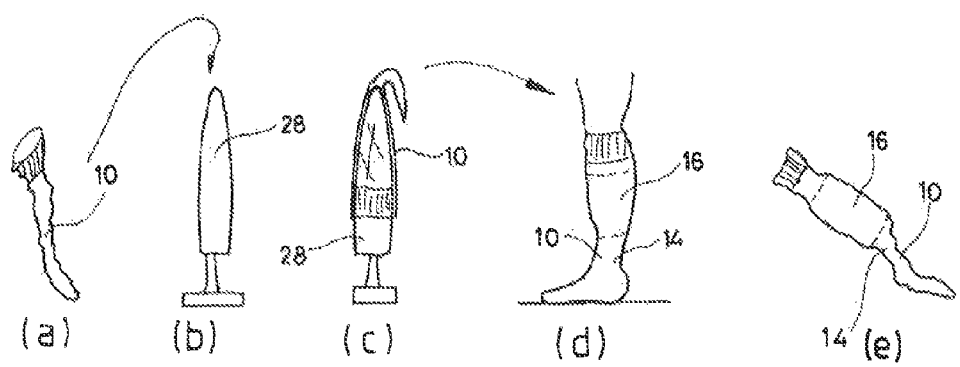
FIG_4
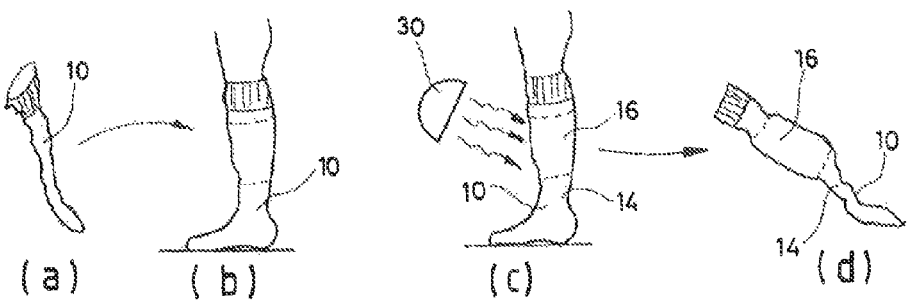
FIG_5

MADE-TO-MEASURE ORTHOSIS FOR COMPRESSION/CONTAINMENT, FOR REINFORCING THE MUSCULO-APONEUROTIC PUMP OF THE CALF

FIELD OF THE INVENTION

The invention relates to elastic venous compression (EVC) orthoses that are indicated in various clinical manifestations of venous insufficiency of the lower limbs.

BACKGROUND OF THE INVENTION

Such orthoses, previously known as "elasticated" stockings or socks or "elasticated" tights, are textile medical devices that produce a therapeutic effect by compression of the lower limbs, in contrast to "posture" stockings (or indeed "support" stockings or "anti-tiredness" stockings), and to "fashion" stockings, which are not medical devices with a therapeutic purpose.

EVC orthoses are designed to produce a therapeutic effect by compressing the lower limb over a greater or lesser extent, usually with a profile that is degressive going upwards from the ankle. Depending on the type of orthosis, the pressure measured at the ankle may lie in the range 10 millimeters of mercury (mmHg) to more than 36 mmHg (i.e. 13 hectopascals (hPa) to 48 hPa, where the unit mmHg is nevertheless in widespread use for measuring pressure in the field of phlebology and medical compression). In France, stockings are subdivided into four textile classes in the ASQUAL system, namely class I (13 hPa to 20 hPa≈10 mmHg to 15 mmHg at the ankle), class II (20 hPa to 27 hPa≈15 mmHg to 20 mmHg), class III (27 hPa to 48 hPa≈20 mmHg to 36 mmHg), and class IV (>48 hPa≈>36 mmHg). These compression classes may be different in other countries.

In order to enable the lower limbs to be subjected to strong compression, such orthoses are made from a knit that presents a texture that is tight to a greater or lesser extent with an incorporated elastic weft yarn, generally a covered spandex.

More precisely, under the effect of being on the limb, the stretch textile of the orthosis exerts compression that results from the return force of the elastic fibers making up the material, and the application of those elastic return forces against the perimeter of the outline generates a local pressure at a given point that is inversely proportional to the radius of curvature at the outline at said point, in application of the Laplace-Young equation.

This pressure is the "textile pressure" as defined and calculated in the meaning of French standard NF G 30-102, part B. The term "pressure" is used in the present description to designate the mean, at a given altitude, of the standardized pressures exerted locally along an outline of the leg (which outline may be circular or elliptical in the approximation of a leg model).

The knit and the yarns, and also the size of the rows of stitches are selected so as to apply predetermined pressures at different altitudes up the lower limb, e.g. at the height of the ankle, at the start of the calf, over the calf, at the popliteal space, etc., all the way up to the top of the thigh, which altitudes are conventionally written B, C, . . . , G. These various pressures are defined for each class with reference to metrological jigs such as the leg model of French standard NF G 30-102 part B, Appendix B, corresponding to the leg model of the "Hohenstein" type in the German reference RAL-GZ 387.

The above-mentioned characteristic of the pressure profile being degressive consists in exerting a maximum pressure at the ankle and then a pressure that is degressive going from the ankle to the calf or to the thigh. It relies on the fact that in the orthostatic situation the intravenous pressure is degressive from the ankle to the calf and to then to the thigh. In the event of chronic venous insufficiency, the elastic compression exerted by the orthosis on the limb induces an anti-stasis effect encouraging venous return.

More precisely, physiologically speaking, the calf is the key element of venous hemodynamics of the lower limbs and of chronic venous pathology.

The importance of the effect of the "muscle pump" or the "calf musculo-aponeurotic pump" (CMAP) have been described in terms of return venous blood flow, where physiological cycles of the calf muscles contracting and relaxing give rise, via opening and closing of valves of the veins, to emptying and filling of the venous network of the lower limb. The efficiency of CMAP decreases progressively with a subject's age, thereby naturally aggregating chronic venous insufficiency.

Chronic venous insufficiency is characterized by a failure of this muscle pump effect. When the insufficiency is severe, the ankle is also involved, because of deep refluxes or by Cockett's perforators, which play a major role in trophic disorders and ulcers.

The starting point of the invention is the search for means enabling the efficiency of the CMAP to be improved or for it to be taken over by a compressive orthosis that is better adapted to this role than are the orthoses that have been proposed in the past.

The prejudice whereby a stocking should exert maximum pressure at the ankle and then pressure that is degressive going from the ankle to the calf or to the thigh is based on the way intravenous pressures are distributed in the orthostatic situation. In that situation, the effect of gravity causes intravenous pressure to be degressive from the ankle to the thigh, whence the need for matching compression.

However, studies on venous physiology, in particular using recent tools for modeling and simulating containment such as those described in WO 2006/087442 A1 (Laboratoires Innothera), show that the effectiveness of an EVC orthosis, providing it is possible to make the CMAP operate, lies rather in improving its efficiency.

FR 2 824 471 B1 (Rodier) describes an approach consisting in providing "elective compression/containment" by means of a multizone stocking with different knits, associating a region with a very elastic knit over the foot and the ankle followed by a region with a knit that presents little elasticity from the bottom of the calf up to the popliteal space, and extended by a region in which the knit is once more very elastic from the knee to the top of the thigh. The basic idea consists in providing zones with a compressive effect (foot, ankle, and thigh) on either side of a zone with an effect that is more one of containment (calf). This zone of the orthosis produces less effect at rest than those on either side of it, however during contractions of the calf muscle it exerts increased compression, thereby increasing the power and reinforcing the emptying effect of the CMAP.

In this respect, it should be specified that the terms "compression" and "containment" define two effects that are clearly different, even though they are sometimes confused in everyday speech:

"compression" is the effect produced by an elastic orthosis both at rest and when making an effort, on a limb segment as a result of more or less strong return forces from the elastic fibers of the orthosis. These forces act in almost constant manner on the limb: at rest, the compression is present at the nominal pressure value and when making an effort the effect of the compression is increased by the contraction of the muscle masses; and conversely, "containment" is the effect produced by an orthosis that acts in different manners between making an effort and being at rest on a limb segment under the action of a structure that is considered as being inelastic, e.g. a non-elastic bandage, also referred to as a "short-stretch bandage". At rest, that type of bandage exerts low or zero pressure; in contrast, during muscular contraction, it opposes local increases in the volume of the calf that comes into abutment against the non-elastic structure, so pressure is thus increased. Containment is thus effective and it is active while making an effort and practically inactive while at rest.

It is in order to distinguish between these two notions that the respective terms "compression" (or "compressive") and "containment" (or "containing") are used.

Concerning these definitions, the proposal of above-mentioned FR 2 824 471 B1 that makes use only of yarns and stitches that are elastic to a greater or lesser extent over the height of the orthosis produces a containment effect level with the calf, but to a very partial extent only.

It comprises rather zones that are all elastic but that present different degrees of elasticity, as has also been proposed in EP 0 934 043 B1 (Couzan) or EP 1 240 880 A2 (Stolk). Those last two documents teach making a stocking or a sock with a zone that is less rigid (more elastic) in the region of the calf, respectively in uniform manner over the entire circumference of the calf, or only in the posterior region thereof.

In addition, from a technological point of view, all of those prior art "multizone" structures are found to be difficult to make in practice, given the difficulty that exists in setting the knitting machine so as to obtain the required variable elasticity profiles, with transitions that are very abrupt between very non-uniform textures that correspond to the different zones of the stocking or the sock.

Furthermore, and above all, those orthoses that may be referred to as "semi-containment" are not specifically adapted to a given patient. Concretely, the practitioner is content merely to select an orthosis from a grid of sizes after measuring the perimeter of the ankle and of the calf. In practice, this leads to a compromise solution that does not take the real morphology of the calf into account, which morphology may vary widely from one patient to another and cannot be described suitably merely by measuring the maximum perimeter of the calf.

This drawback is particularly troublesome with products that are supposed to produce a containment effect, since the reinforcement of the effect of the CMAP depends on the non-elastic structure being a good fit to the limb segment in question, over the entire extent thereof: if the non-elastic structure is not in close contact with the limb at rest, then it will procure very little effect for a small or moderate increase in the volume of the muscle; on the contrary, if it is too small, then it will exert stress on the limb even at rest, with harmful effects on blood circulation, in addition to providing the wearer with a binding effect that runs the risk of making the orthosis particularly uncomfortable for the patient.

It thus appears to be desirable to be able to make orthoses that provide a genuine containment effect on the calf via a structure that is not elastic (as opposed to a structure of reduced elasticity) and that fits the exact morphology of the limb segment of each patient.

If it is desired to have a containment product that is rigid and made-to-measure, specifically fitting the patient, a first solution consists in using multilayer bandages, with the well-known difficulty of adjusting the bandage properly, since it must not be too tight (which would squeeze the calf) nor too loose (which would not produce any effect), thereby producing a result that is highly "operator-dependent". As explained above, the fitting of a rigid containment product is highly critical, unlike a compressive elastic structure which is much more tolerant.

In addition, the bandage needs to be readjusted regularly, and on each occasion with the same care in order to secure a good fit.

For these reasons, patients generally prefer to use some other solution, in the form of a knitted orthosis for putting on in more convenient manner and of better appearance.

The problem is then that of fabricating a product that is rigid and made-to-measure, being an exact fit to the particular morphology of the patient. The technique consists in taking the most complete possible measurements of the calf, with circumferences at several altitudes. The orthosis is then knitted on a flat knitting machine and is shaped by sewing a seam all along its length, thereby requiring an additional manufacturing step. It can be understood that such a complete made-to-measure technique is lengthy to implement, complicated, and therefore expensive, and it does not enable rigid containment products to become widespread, in spite of their manifest therapeutid advantages.

OBJECT AND SUMMARY OF THE INVENTION

The problem of the invention is thus to be able to make a containment orthosis (a rigid product) that is in the form of a final "made-to-measure" product, i.e. that is a good fit to the patient's morphology, but without that requiring it to be fabricated using conventional lengthy and expensive "made-to-measure" techniques.

In particular, the invention can be implemented i) on a circular knitting machine (and not a flat knitting machine, which would require an additional manufacturing step for sewing the seam), and ii) making a product that is standard, thus suitable for being fabricated at reasonable cost and in large quantities.

And this is done with a new EVC orthosis structure:
that reinforces the beneficial effects of the CMAP by appropriate containment of the calf;
that is technologically easy to make; and
that can easily be fitted to the very wide variety of leg morphologies that are to be encountered in the population of patients concerned.

It can also be seen that the invention makes it possible to obtain an EVC orthosis for the lower limb that no longer provides more or less strong compression on the calf, but genuine containment, by placing an essentially rigid element around the calf, i.e. an element that is not elastically deformable. In addition, this great rigidity at the calf (containment effect) is associated with low rigidity at the ankle (compression effect).

Great rigidity at the ankle is considered as means for optimizing the CMAP, which constitutes the main driver of venous return in the lower limbs.

Great rigidity at the calf needs to be associated with small rigidity (and thus high deformability) at the ankle in order to make it easy to put on, take off, and accept the product—in particular in order to avoid excessive compression that would rapidly become intolerable, in particular for a patient who is bedridden or inactive.

The term "rigidity" is used herein in the meaning of the definition of the European pre-standard XP ENV 12718:2001, i.e. the "increase in compression per centimeter of increase in leg circumference, expressed in hectopascals per centimeter and/or in millimeters of mercury per centimeter".

The idea on which the invention is based consists in making a compressive orthosis by conventional techniques, while incorporating therein a containment portion that is obtained by incorporating an "intelligent" fiber in the portion of the orthosis that covers the calf, which fiber has mechanical characteristics that can be modified by subsequent action, e.g. thermal action.

In its original state (before being activated), the structure is flexible, thereby enabling the orthosis to be knitted in conventional manner on a circular knitting machine.

After activation, e.g. by applying heat, the "intelligent" fiber is made to be stretchable, thereby making it easy to put the product on and in particular guaranteeing that it adapts perfectly to the shape of the patient's calf. It then transforms into a rigid fiber, e.g. on cooling. The resulting product is thus an accurate fit to the shape of the patient's calf, and therefore enables effective containment to be applied to the calf by means of a containment portion of a shape that is adjusted to match the morphology of the calf, this portion being, so to speak, "molded in place" on the patient's calf. This containment portion over the calf region is associated with a conventional compressive portion over the remainder of the leg, and in particular over the ankle region.

In a field that is related but different, EP 0 272 989 A1 (Richard Freres SA) proposes subjecting a zone of an elastic support textile article (e.g. an orthopedic knee pad) to localized application of heat so as to shrink the synthetic knit yarns in that zone. Heat is applied on only one face of the article, e.g. by placing it on a hot plate, the opposite face remaining intact. The thermal shrinkage of the synthetic yarn of the knit then causes the (elastic) weft yarn that is inserted between the stitches of the knit to be blocked, and consequently reduces or eliminates the elasticity of the textile on its face that was exposed to heat, while conserving that elasticity on its opposite face. That technique makes it possible in particular to make openings for the projecting portions of joints, e.g. around the knee cap for a knee pad. It is thus possible to provide support around the knee cap that is different from the remainder of the article, thereby enabling the knee cap to be isolated from the remainder of the knee pad while having an opening that is well pressed against the knee cap.

More precisely, the invention proposes an EVC orthosis having the same purpose as above-mentioned FR 2 824 471 B1, i.e. a medical compressive orthosis in the form of a sock, a stocking, or tights for the purpose specifically of acting on CMAP.

In a manner that is itself known, such an orthosis comprises: i) an elastic compressive distal portion suitable for covering the ankle and extending to just before the beginning of the calf, to the level of the point where the Achilles tendon joins the calf muscles; and ii) a containment proximal portion extending the compressive distal portion and adjacent thereto in such a manner as to cover the periphery of the region of the calf extending between the level of the junction point between the Achilles tendon and the calf muscle and the level situated beneath the tibial tuberosity.

The distal portion is made by knitting a knit yarn and a weft yarn, the dimensioning and the nature of the knit and the weft yarns and the structure of the knit being selected in such a manner as to exert in a circumference direction, once the orthosis has been put into place on the limb, an elastic return force suitable for producing compression of the limb at a desired therapeutic pressure level. The containment proximal portion is a deformable tubular portion that is knitted in continuity with the elastic compressive distal portion.

In a manner that is characteristic of the invention, the containment proximal portion is essentially non-elastic; and is made by knitting a weft yarn and a knit yarn, one of said weft and knit yarns comprising a thermoformable yarn.

Most advantageously, the compressive distal portion is made by knitting a weft yarn and a first knit yarn, and the adjacent proximal portion is made by knitting the same weft yarn and a second knit yarn comprising said thermoformable yarn, said second knit yarn being used as a replacement for or in addition to the first knit yarn.

The knit yarn may in particular be spandex with a polyamide and/or cotton covering, and the weft yarn may be spandex with a polyamide and/or cotton covering.

The proximal portion may be a portion presenting great rigidity level with the maximum circumference of the calf, lying in the range $15\pm2$ mmHg/cm ($\approx20\pm2$ hPa/cm), or moderate rigidity, lying in the range $5\pm2$ mmHg/cm ($\approx7\pm2$ hPa/cm).

The elastic compressive distal portion may be a lightly compressive portion suitable for exerting a pressure in the range 10 mmHg to 20 mmHg (13 hPa to 27 hPa), or a moderately compressive portion suitable for exerting a pressure lying in the range 20 mmHg to 30 mmHg (27 hPa to 40 hPa) at the level of the minimum circumference of the ankle.

The invention also provides a specific method of making-to-measure a medical compression/containment orthosis for the lower limb so that it fits the leg of a patient. The method comprises the following steps: obtaining an orthosis as described above; heating the orthosis to a temperature that is not less than the activation temperature of the material of the thermoformable yarn for a predetermined duration, the orthosis then being in a freely stretchable state; putting the orthosis onto the patient's leg; cooling the orthosis in situ on the patient's leg; and removing the orthosis in its finished state. The orthosis in its finished state presents a containment proximal portion that is made rigid by said activation, and has a shape and dimensions that fit the corresponding dimensions of the patient's calf, enabling said containment proximal portion to engage closely around the shape of the calf.

If the heating of the orthosis takes place before it is put on the leg, the step of heating the orthosis is implemented by means of a heating former on which the orthosis is initially put into place, with the orthosis once heated being removed from the former in order to be put onto the leg.

Conversely, if the orthosis is put on the leg before being heated, then the heating step is implemented by means of a source of heat directed towards the leg on which the orthosis has already been put.

The invention also provides a specific method of fabricating a medical compressive/containment orthosis for the lower limb as described above. The method comprises successive steps that are executed continuously one after another of knitting the elastic compressive distal portion from a knit yarn and a weft yarn, and of knitting the containment proximal portion from a weft yarn and a knit yarn, one of said weft or knit yarns of the containment proximal portion comprising a thermoformable yarn.

Advantageously, the method comprises: knitting the elastic compressive distal portion from a weft yarn and a first knit yarn; and knitting the containment proximal portion from the same weft yarn and a second knit yarn comprising said thermoformable yarn, the second knit yarn being used as a replacement for or in addition to said first knit yarn.

BRIEF DESCRIPTION OF THE DRAWINGS

There follows a description of an embodiment of the invention given with reference to the accompanying drawings in which the same numerical references are used from one figure to another to designate elements that are identical or functionally similar.

FIG. 1 is an overall view of an orthosis of the invention, in the free state.

FIG. 2 is an elevation view of the same orthosis being worn on a limb, with the various standardized altitudes for measuring the pressures applied by the orthosis to the limb being marked.

FIG. 3 is a macroscopic view describing the structure of the transition zone between the non-elastic containment proximal portion and the elastic compressive distal portion of the orthosis.

FIG. 4 shows the successive steps of the method implemented in the invention for making an orthosis of the invention match the measurements of the patient's leg.

FIG. 5 shows a variant implementation of the FIG. 4 method.

MORE DETAILED DESCRIPTION

In FIGS. 1 and 2, reference 10 is an overall reference for the orthosis of the invention, which is a knitted orthosis made using conventional methods on a circular knitting machine. The orthosis 10 is tubular in shape, comprising a portion 12 that surrounds the foot and a portion of the leg, with a distal portion 14 that surrounds the ankle, and a proximal portion 16 that surrounds the calf. The assembly extends up to a level situated below the knee, when the orthosis is a "knee-high" (or "long") sock. The orthosis is then terminated by a terminal knitted portion 18 of the ribbed type.

This sock-shaped configuration is not limiting, and the invention may also be implemented in the form of a thigh-length sock, being extended by a compressive thigh portion 20. The orthosis of the invention may also be implemented in the form of tights, and/or it need not have a foot portion 12 ("footless" type stocking or tights).

The various adjoining portions of the above-described orthosis are knitted continuously on a circular knitting machine, i.e. making the orthosis does not require any manufacturing step involving assembling distinct parts, naturally with the exception of the operations of stitching the toe of the foot part 12, if there is one.

FIG. 2 shows the various altitudes of the lower limb as defined by the morphological reference specified in the introduction (the "Hohenstein" leg model) in standard notation:

B: ankle, at the point of its minimum circumference;

B1: junction point between the Achilles tendon and the calf muscles;

C: calf, at the point of its maximum circumference;

D: immediately below the tibial tuberosity (i.e. just below the knee);

E: at the center of the knee cap and above the back of the knee (i.e. level with the popliteal space);

F: middle of the thigh; and

G: top of the thigh.

The calf is the segment of the limb that extends between levels B1 and D, and the ankle is the segment of the limb that is situated below level B1.

The pressure exerted at altitude B (at the minimum perimeter of the ankle) is the pressure prescribed for the selected standardized class (I, II, III, or IV).

The pressure values may be read, for example using a dynamometer in application of above-mentioned standard NF G 30-102 part B, after the orthosis has been put onto a reference jig such as the Hohenstein leg model prescribed by that standard.

The pressure exerted on the ankle at the point of its minimum circumference (level B) by the elastic compressive distal portion 14 must be an effective therapeutic pressure. The following values may be retained, depending on the needs of the patient:

10 mmHg to 20 mmHg (13 hPa to 27 hPa) for relatively light compression of the ankle; and 20 mmHg to 30 mmHg (27 hPa to 40 hPa) for moderate compression of the ankle.

The elastic compressive distal portion 14 that produces these therapeutic pressures is made using a knit of more or less tight texture with an incorporated elastic weft yarn, e.g. by using:

for the weft yarn, a yarn of spandex or a mixture of spandex and elasto-diene (synthetic rubber latex), with a polyamide and/or cotton covering; and as the knitting yarn, likewise spandex with a covering of polyamide and/or cotton, preferably having a weight per unit length that is less than that of the weft yarn.

In a manner characteristic of the invention, the proximal portion 16 is a containment portion (i.e. it is essentially non-elastic after activation), of tubular shape, and it extends:

vertically: over the extent of the calf, i.e. over the region extending from the level B1 (junction between the Achilles tendon and the calf muscles) and the level D (below the knee), or at least over the major fraction of this region; it should be observed that the ankle (region extending around the level B) never forms part of this region that is covered by the proximal portion 16; and in the circumference direction: over the entire periphery of the calf.

This non-elastic portion is made to measure, in the manner that is explained below, i.e. it presents an external configuration that is an accurate fit to the shape and the dimensions of the patient's calf. As a result, once the orthosis has been put on the limb, this portion exerts the looked-for containment effect, i.e. at rest it exerts essentially no containment force, but when making an effort it opposes the limb with stiffness that provides the containment effects at the desired degree of effectiveness.

Concerning the rigidity $R_c$ of this containment proximal portion 16, it is possible to use the following values (in accordance with the above-mentioned European pre-standard XP ENV 12718:2001):

for strong containment:

$Rc=15\pm2$ mmHg/cm ($\approx 20\pm2$ hPa/cm)

for moderate containment:

$Rc=5$ mmHg/cm ($\approx 7$ hPa/cm)

These values for $R_c$ are measured at the altitude C, i.e. at the point where the calf has its maximum circumference.

By acting separately both on the elasticity of the compressive distal portion 14 over the ankle and on the rigidity of the containment proximal portion 16 over the calf, it is possible to combine several compression/containment effects, for example:

weak compression of the ankle with strong containment of the calf;

moderate compression of the ankle with strong containment of the calf;

weak compression of the ankle with moderate containment of the calf; or moderate compression of the ankle with moderate containment of the calf.

According to another characteristic aspect of the invention, the non-elastic containment proximal portion 16 is made by selectively incorporating in the region corresponding to said portion a yarn of thermoformable polymer, i.e. a yarn that can be stretched by applying heat for a predetermined duration.

Most advantageously, the distal and proximal portions 14 and 16 are knitted continuously in a single sequence on the knitting machine, thereby avoiding any manufacturing step of assembling separate parts.

Provision is merely made, on going past the boundary between the two portions 14 and 16, to incorporate in the knitting a replacement of the knitting yarn by the above-mentioned thermoformable yarn. This operation may be performed continuously, without interrupting the operation of the knitting machine.

The weft yarn remains the same both in the distal and in the proximal portions 14 and 16.

With the example of the yarns specified above for the elastic compressive distal portion 14, the proximal portion 16 is thus knitted with:
- as its weft yarn, the spandex yarn having a polyamide and/or cotton covering; and
- as its knitting yarn, the lower weight spandex yarn having a polyamide and/or cotton covering, together with a second yarn of thermoformable polymer.

A thermoformable yarn suitable for implementing the invention is for example made on the basis of Thermoform LXN (registered trademark) produced by the supplier Orfit Industries. It is a yarn constituted by a spun polymer with a flexible monofilament of poly-c-caprolactone, having mechanical properties that can be modified by applying a temperature of 65° C. for about one minute.

That yarn presents the advantage of being suitable for use as a standard yarn in a conventional knitting machine, thus enabling the machine to be used conventionally, without any particular modification.

The effect of the activation step is to soften the monofilament that becomes flexible while it is hot and that stiffens on cooling.

During activation, the textile incorporating the thermoformable yarn may be molded in position on any suitable former. After cooling, the textile hardens and retains the configuration of the former on which it was applied. Poly-c-caprolactone presents the advantage of having an activation temperature that is relatively low (60° C. to 70° C.) and of remaining moldable so long as it remains at a temperature that is situated above its crystallization temperature, in particular down to 40° C. to 45° C., thereby giving very wide latitude for molding, in particular on a portion of the body without running the risk of excessively high temperatures.

EP 2 050 848 A2 (Orfit Industries) describes a hybrid textile made by interleaving such a thermoformable yarn with a non-thermoformable yarn constituting the support of the textile. The thermoformable fiber ensures that the textile is suitable for molding, while the non-thermoformable fiber provides structure and support to the textile and contributes to increasing the stiffness and the stability of the resulting final product.

That patent describes in particular how the initial shrinkage of the thermoformable fiber at the moment of activation is compensated by the stiffness obtained by the non-thermoformable structural fibers, thereby enabling the textile to be released of any undesirable internal stress after cooling, and enabling it to be retain the configuration of the former on which it was applied.

FIG. 3 shows more precisely how the thermoformable yarn is incorporated in the structure of the knit for making the containment proximal portion.

This figure shows the knit structure at the boundary between the elastic compressive distal portion 14 and the rigid containment proximal portion 16. The transition is achieved simply by changing the knit yarn without changing the parameters to which the knitting machine is set. The knit structure is thus the same over the entire extent of the leg portion of the orthosis.

The weft yarn 22 is the same in both portions, for example double spandex with polyamide covering. The knit yarn 24 of the elastic portion 14 may, for example, be single or double spandex with polyamide covering, while the knit yarn 26 in the rigid portion 16 may for example be a plied yarn made up of a double Thermoform LXN core yarn with a polyamide covering.

The product may be knitted using conventional techniques on a conventional circular knitting machine, such as a Santoni knitting machine.

The above indications are naturally given by way of example and have no limiting character.

FIG. 4 shows the method of "fitting to the wearer" that enables an orthosis of the invention made in the manner described above to have its containment proximal portion 16 made to measure so as to be an accurate fit to the dimensions and the shape of the patient's calf.

After being knitted in conventional manner, the orthosis 10 is initially in the form of a standard product, i.e. a product that is not made to measure (step a); it is merely provided like any conventional EVC orthosis and even like any garment, in appropriate standard sizes, suitable for selection from a grid of dimensions.

The orthosis 10 is then put onto a hot blade 28 of elongate shape (step b) which raises the entire product to a temperature of 60° C., and in particular its containment portion 16 (step c). At this temperature, the containment proximal portion takes on a softened consistency because the thermoformable yarn has been activated.

The patient then puts on the orthosis (step d) and massages it on the leg, in particular on the calf, so that the proximal portion 16 becomes a perfect fit to its curve in as uniform a manner as possible.

After cooling, the orthosis may be taken off (step e). It will then have taken on its final "made-to-measure" shape, with a containment proximal portion 16 that has become rigid, taking on a shape that is a good fit to the shape and the dimensions of the patient's calf, and an elastic compressive distal portion 14, thereby producing a product that associates high rigidity at the calf (containment proximal portion 16) with low rigidity at the ankle (elastic compressive distal portion 14), while ensuring that the lower limb is compressed at a therapeutic level.

FIG. 5 shows a variant implementation of the method of making to measure as described above.

In this variant, the orthosis 10 in its initial state (step a) is put in that state on the patient's leg (step b), and it is in this configuration that heat is applied (step c) by a heater appliance 30, e.g. a hairdryer or a source of infrared radiation, the heat being directed towards the proximal portion 16 around the calf. The patient massages the orthosis on the leg and allows it to cool in situ. After cooling, the orthosis may be taken off and it is then in its final state (step d) of being made to measure for the patient.

What is claimed is:

1. A method of making-to-measure a medical compression/containment orthosis of the lower limb to fit a patient, the method comprising the following steps:
    obtaining an orthosis comprising
    i) an elastic compressive distal portion suitable for covering the ankle and extending to just before the beginning of the calf, to the level of the point where the Achilles tendon joins the calf muscles and being made by knitting a knit yarn and a weft yarn, the dimensioning and the nature of the distal knit and the distal weft yarns and the structure of the knit being selected in such a manner as to exert in a circumference direction, once the orthosis has been put into place on the limb, an elastic return force suitable for producing compression of the limb at a desired therapeutic pressure level, and ii) a containment proximal portion extending the compressive distal portion and adjacent thereto in such a manner as to cover the periphery of the region of the calf extending between the level of the junction point between the Achilles tendon and the calf muscle and the level situated beneath the tibial tuberosity and being a deformable tubular position knitted continuously with the elastic compressive distal portion by knitting a weft yarn and a knit yarn, one of the proximal weft and proximal knit yarns comprising a thermoformable yarn;

heating the orthosis to a temperature that is not less than the activation temperature of the thermoformable yarn for a predetermined duration, the orthosis then being in a freely stretchable state;

putting the orthosis onto the patient's leg;

cooling the orthosis in situ on the patient's leg; and removing the orthosis in its finished state;

the orthosis in its finished state presenting a containment proximal portion that has been made rigid by said activation, and having a shape and dimensions that fit the corresponding dimensions of the patient's calf, enabling said containment proximal portion to engage closely around the shape of the calf.

2. The making-to-measure method of claim 1, wherein the step of heating the orthosis precedes the step of putting it onto the leg, and wherein the step of heating the orthosis is implemented by means of a heating former on which the orthosis is initially put into place, with the orthosis once heated being removed from the former in order to be put onto the leg.

3. The making-to-measure method of claim 1, wherein the step of putting the orthosis on the leg precedes the step of heating the orthosis, and wherein the heating step is implemented by means of a source of heat directed towards the leg on which the orthosis has already been put.

* * * * *